United States Patent
Perozziello et al.

(10) Patent No.: US 6,599,132 B1
(45) Date of Patent: Jul. 29, 2003

(54) SCANNING CAPACITANCE SAMPLE PREPARATION TECHNIQUE

(75) Inventors: Eric Anthony Perozziello, Half Moon Bay, CA (US); Guanyuan Michael Yu, San Jose, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 09/451,463

(22) Filed: Nov. 30, 1999

(51) Int. Cl.$^7$ .......................... G01R 31/26; H01L 21/66
(52) U.S. Cl. ............................ 437/17; 438/14; 438/18
(58) Field of Search ............................. 438/14, 17, 18

(56) References Cited

U.S. PATENT DOCUMENTS 5,456,111 A * 10/1995 Hulsing, II

* cited by examiner

*Primary Examiner*—Long Pham
(74) *Attorney, Agent, or Firm*—Michael Hetherington (57) ABSTRACT

Currently semiconductor processing and device manufacturing relies heavily on continued scaling of critical dimensions for cost reduction and performance enhancement. In order to continue this scaling below 0.1 micron with acceptable manufacturing yields, reliable measurement of electrical charge distribution and the placement of dopants is essential, yet no conventional technique exists to obtain distortion-free cross-sectional images. An aspect of the invention relates to a technique for forming a precisely-located, substantially atomically smooth cross-section of a crystalline sample suitable for Scanning Capacitance Microscopy analysis. Another aspect of the invention provides a method for deconvolving Scanning Capacitance raw data into an accurate representation of electrical carrier distributions suitable for the higher resolution attainable with the new sample preparation technique.

8 Claims, 10 Drawing Sheets

SCANNING CAPACITANCE SAMPLE PREPARATION TECHNIQUE

GOVERNMENT SUPPORT

This invention was made with government support under contract DABT63-94-C-0055 awarded by Defense Advanced Research Projects Agency. The government has certain rights in this invention.

FIELD OF THE INVENTION

The field of the present invention relates generally to a technique for cross-sectioning a crystalline material to provide a substantially atomically smooth surface. In particular, the field of the invention relates to preparation of semiconductor samples for Scanning Capacitance Microscopy (SCM), Scanning Tunneling Microscopy (STM) or other analysis techniques.

BACKGROUND

Many material analysis techniques require a sample to be cross-sectioned; that is, to be sliced in a direction substantially different than the planar surface. The semiconductor industry typically builds devices in a planar fashion, using thin-film techniques. As semiconductor devices shrink to sub-micron, and beyond sub 0.1 micron critical planar dimensions, analysis techniques for two-dimensional, cross-sectional images have become inadequate.

Much of the economic success of the semiconductor industry depends on the continued shrinking of devices, which makes circuits faster and more compact, while lowering the cost. Microprocessor and DRAM device dimensions have shrunk from critical dimensions of approximately 0.8 microns in 1990 to 0.18 microns in 1999.

It is currently possible to build devices for which there is no conventional way to obtain substantially accurate images of two dimensional dopant profiles. This impediment increases the difficulty in designing the next generation of smaller devices, since process or device improvements rely on knowledge of device geometries and electrical carrier distributions. Device design is typically an iterative process, where a prototype device is built, then tested and studied, and then the design is improved based on the knowledge gained from the first prototype. This design loop can occur several times before a production design is finished.

Additionally, Computer Aided Design (CAD) tools specific to the semiconductor industry rely on physical model development and calibration for predictive modeling of device designs before the actual devices are built. Therefore, part of the design loop involves CAD modeling, and those CAD models rely on accurate measurement of test devices.

A semiconductor electronic device operates by controlling the position and motion of charge carriers, typically electrons and holes. Dopants are introduced into a crystalline semiconductor material to locally supply carriers and to affect their behavior when the device is electrically operated. The designer of such devices must be able to create a process to place the dopants with spatial accuracy to optimize the device performance. As devices are shrunk to improve performance, dopant placement accuracy is vital to obtaining working devices and acceptable manufacturing yields.

Techniques for dopant profiling have been largely limited by two-dimensional spatial resolution. One dimensional techniques, such as Secondary Ion Mass Spectrometry (SIMS) have high spatial resolution in the depth dimension, but require areal dimensions larger than most semiconductor devices of interest. Cleave-and-Stain techniques provide two-dimensional images, but spatial resolution is far from adequate for modern device dimensions, and quantization of dopant concentration is severely limited. Conventional spreading resistance techniques are also limited in spatial resolution to dimensions much larger than most devices of interest today. Higher spatial resolution is needed for two dimensional, cross-sectional analysis techniques.

Scanning Capacitance Microscopy (SCM) is a fairly recent development for high spatial resolution images of electrical charge concentrations, which can represent the electrically active dopant concentration in the $1 \times 10^{15}$ to $5 \times 10^{21}$ per cubic cm range. Scanning Capacitance Microscopy apparatus is explained in U.S. Pat No. 5,065,103, which is incorporated herein by reference. This measurement technique uses an Atomic Force Microscope (AFM) apparatus, combined with a high-frequency capacitance sensor to extract local capacitance versus electrical potential (dC/dV) information. By scanning the AFM/SCM tip in two dimensions and processing dC/dV information, a spatial image of electrical charge concentrations is obtained. This technique can image the charge concentrations in two dimensions across the surface of a sample. No information of charge concentrations in the depth dimension is obtained with this method.

Sample Preparation

Researchers at Texas Instruments, University of Texas, Intel, University of Utah, Digital Instruments, The National Institute of Standards and others have used standard techniques for cleaving, and mechanically polishing the cleaved surface for two-dimensional imaging with one dimension being substantially orthogonal to the sample surface. H. Edwards, et. al., "Scanning Capacitance Spectroscopy: An analytical technique for pn-junction delineation in Si devices," *Appl. Phys. Lett.*, 72, 698 (1998) and A. Erickson, et. al., "Quantitative Scanning Capacitance Microscopy analysis of Two-Dimensional dopant concentrations at nanoscale dimensions," *J Elec. Mat.*, 25, 301 (1996), U.S. Pat. No. 5,710,052, and U.S. Pat. No. 5,520,769 are incorporated herein by reference. The technique depends on conventional methods normally employed for Transmission Electron Microscopy (TEM) or Scanning Electron Microscopy (SEM) sample preparation. Mechanical polishing produces an undesirable atomically rough surface, which adds noise and degrades spatial resolution and quantization of charge. The cleaving process is very imprecise, therefore making the selection of a specific device for analysis difficult or impossible. Also, cleaving a wafer is destructive at the wafer level, severely restricting further processing of that wafer. Therefore, this technique is not practical as an in-situ process monitor since an entire wafer must be broken in order to analyze one process step.

Another example of a conventional attempt to solve the problem is a technique used by Charles Evans and Associates. K. J. Chao, et. al., "Applications of AFM and SCM in Semiconductor Devices," Charles Evans and Associates Analytical Measurement Conference, Sunnyvale, Calif. 1999, incorporated herein by reference. They have developed a technique wherein a device is selected by photolithography. Plasma etching is then used to form an orthogonal surface which cross-sections the device of interest. The resulting structure resembles a pillar or thin vertical wall. The pillar or wall on which the cross-section exists is toppled so as to provide direct topside access to the orthogonal, cross-sectional surface. Mechanical polishing can be used on this newly formed surface if the toppled structure is mechanically secured to the wafer or another substrate. SCM is then used to image the charges in the cross-section of a device. A major disadvantage of this technique is that the cross-sectional surface is atomically rough since it was formed with plasma etching and possibly a subsequent mechanical polish. This has the undesirable effect of adding noise, degrading spatial resolution and quantization of charges. Another disadvantage of this approach is that each pillar containing a selected device for analysis must be manually toppled and secured to a substrate. Furthermore, an electrical ground must be provided for the small, toppled piece. Such intricate handling of small parts may introduce contamination and measurement errors, and requires additional preparation time by a skilled, dexterous person.

What is needed is a sample preparation technique to produce a substantially atomically smooth surface at an angle to the original sample surface, without breaking the entire wafer. It is also desirable to specifically select one or more devices for analysis, while leaving other devices on the wafer undisturbed. Furthermore, it would be desirable to select a specific portion of or exact location on specific devices. It would be advantageous to eliminate the handling or anchoring of small parts, and to be able to prepare many devices on a substrate for analysis at once, without operating on each device individually.

Deconvolution

Once conventional SCM is used to measure capacitance versus electrical potential for each spatial scan point, this data must be converted to obtain corresponding electrical charge concentrations.

Conventional models have simplified the interaction of the SCM tip with the sample by using a one-dimensional, two-dimensional or quasi-three-dimensional structure. J. J. Kopanski, et. al., "*Scanning Capacitance Microscopy Measurements and Modeling: Progress toward dopant profiling of silicon,*" J. Vac. Sci. Technol. B, 12, 242 (1996) and J. F. Marchiando, et. al., "*Model Database for Determining Dopant Profiles from Scanning Capacitance Microscopy Measurements,*" J. Vac. Sci. Technol. B, 16, 463 (1998), incorporated herein by reference.

Furthermore, conventional models have assumed that charge concentrations in the vicinity of each spatial sample point are uniform over the region of the sample influenced by the electrical potential of measurement tip. This assumption causes significant errors when the charge concentration gradient is large, such as gradients necessary in 0.18 micron and smaller transistors. One solution to this shortcoming, disclosed in U.S. Pat. No. 5,523,700 and incorporated herein by reference, uses a specialized feedback system to cause the scan to occur along iso-concentration paths, thus mapping contours of carrier concentration. This technique, however, requires specialized or modified equipment.

Another shortcoming of some conventional techniques is that they do not account for the actual radius of the SCM tip. Rather, these conventional models assume that the SCM tip is atomically sharp or a perfect point source for the applied potential.

Additionally, if the SCM tip is not oriented orthogonal to the surface, which may occur when measuring the aforementioned anisotropically etched surface, then the sidewall of the tip will electrically influence a region of the sample adjacent to the region directly under the tip. This angular tilt also causes a measurement error.

For accurate deconvolution of SCM data, what is needed is a technique for cataloging various physical scenarios with each corresponding SCM response, and a method for iterating on cataloged parameters to find the actual distribution of electrical charge from measured SCM data.

SUMMARY

In order to overcome the above-discussed disadvantages of conventional sample cross-sectioning techniques, one aspect of the present invention utilizes the fact that certain etch chemistries are capable of anisotropically etching crystalline materials selectively, substantially stopping precisely on certain crystalline planes of atoms. A further aspect is that this etch process can be masked in selected regions so as to protect desired areas of a sample from the etch, while allowing other areas to be subjected to the etch. The etched region is bounded by the masked or lithographically defined region in the plane of the original sample surface, and is bounded in the depth direction by a crystallographic plane that serves as an etch stop. The angle of the newly-formed surface corresponding to the crystallographic plane relative to that of the original sample surface will depend on the specific crystal structure, and the specific etch chemistry. Additional polishing or smoothing of the surface can be accomplished using chemistries and techniques known to those skilled in the art to improve surface quality.

For example, if the substrate material is silicon with a starting surface having crystal orientation of <100>, and the etchant is Potassium Hydroxide (KOH) based, then the etch will substantially stop on the <111> silicon crystal plane. This produces an angle between the original surface and the newly formed cross-sectional surface of 54.7 degrees, since the inverse-cosine of the normalized mathematical dot product between (1,0,0) and (1,1,1) is 54.7 degrees. In a preferred embodiment, Ammonium Fluoride chemistry is then used to improve surface quality by minimizing remaining asperities on the <111> plane.

In accordance with another aspect of the present invention, specific devices or specific regions of specific devices can be selected using conventional photo- or electron-beam lithography. The selected devices and/or device regions are not necessarily selected at random. Additionally, many devices on a common substrate or wafer can be selected, patterned and etched at once, with a single lithographic mask or pattern using conventional methods known to those skilled in the art.

It will be appreciated that an aspect of the present invention utilizes anisotropic chemical etching and polishing to form a substantially atomically smooth surface apart from the starting sample surface and does not rely on mechanical polishing or the like. Therefore an aspect of the present invention provides previously unattainable true and clear images of electrical charge concentrations beneath the original sample surface in sub-micron devices. An aspect of the invention can be applied to other analysis techniques where a substantially atomically smooth cross-sectional surface is necessary or desirable.

A further aspect of the present invention is that the technique is non-destructive at the wafer or substrate level. A production wafer or substrate can incorporate many devices intended for testing and measurement purposes, not essential for final circuit operation. These test devices may be destroyed in the testing process using an aspect of the present invention, thereby serving as in situ monitors, or quality control devices. The results obtained from the testing of these devices may provide critical information needed to detect faults in manufacturing equipment, or errors made in prior processing steps. Nevertheless, the wafer on which these test devices reside can remain intact, and may be continued through completion of the manufacturing process after testing with an aspect of the present invention.

Because one aspect of the present invention allows testing at a specific location, automated testing is possible. In conventional methods, there are problems associated with either locating a specific device, or with tedious handling of small pieces separated from the original substrate. Another aspect of the present invention is that it allows economical device testing and analysis in a semiconductor fabrication facility using conventional laboratory equipment. Many points or devices on a substrate can be analyzed without adding significant cost, making high quality, across-the-wafer uniformity measurement inexpensive.

Another aspect of the present invention is that the angle between the original sample surface and the new, cross-sectional surface is precisely defined by the crystal geometry. This allows precise trigonometric scaling of at least one of the dimensional axes to provide an image that is representative of an orthogonal cross-section. Said angle need not be orthogonal to the original sample surface, which provides an effective magnification along at least one dimension, enhancing spatial resolution. Proper calibration of this dimension to a "depth" scale is a simple trigonometric conversion.

The present invention is compatible with a variety of lithographic and masking techniques. For instance, optical, x-ray, e-beam, or direct-write AFM lithography can be used for patterning purposes in accordance with an aspect of the present invention. Furthermore, an aspect of the invention is compatible with a variety of measurement or analysis techniques such as Scanning Electron Microscopy (SEM), Scanning Tunneling Microscopy (STM), 4-point probe measurement, Auger Electron Spectroscopy (AES), Rutherford Backscattering (RBS), and various other methods where a smooth cross-section of a crystalline sample is useful or necessary.

A variety of scanning probe measurement techniques that can be applied to surfaces or near-surface regions are similarly applicable to an aspect of the present invention.

In order to overcome disadvantages of conventional SCM deconvolution techniques, an aspect of the present invention provides a database of structure parameters (tip tilt, oxide thickness, average concentration, concentration gradient, tip radius and tip DC bias) and corresponding theoretical dC/dV values. This database is then applied iteratively to determine accurate two-dimensional electrical charge concentrations from measured SCM data. Because there may exist multiple nodes in the database that match the measured data at a particular pixel or spatial scan point, data from neighboring pixels is incorporated in the selection of the appropriate matching node.

Said database is populated with theoretical data by simulating the electrical response from various tip/sample structures in a conventional three-dimensional electrical device simulator implementing relevant conventional electrostatic equations. "*Davinci User's Manual*," Technology Modeling Associates Inc. (1996) incorporated herein by reference.

BRIEF DESCRIPTION OF THE DRAWINGS

These and other features, aspects and advantages of the present invention may be appreciated from the following detailed description and appended claims together with the accompanying drawings in which:

DETAILED DESCRIPTION

Conventional SCM

Figure 1:
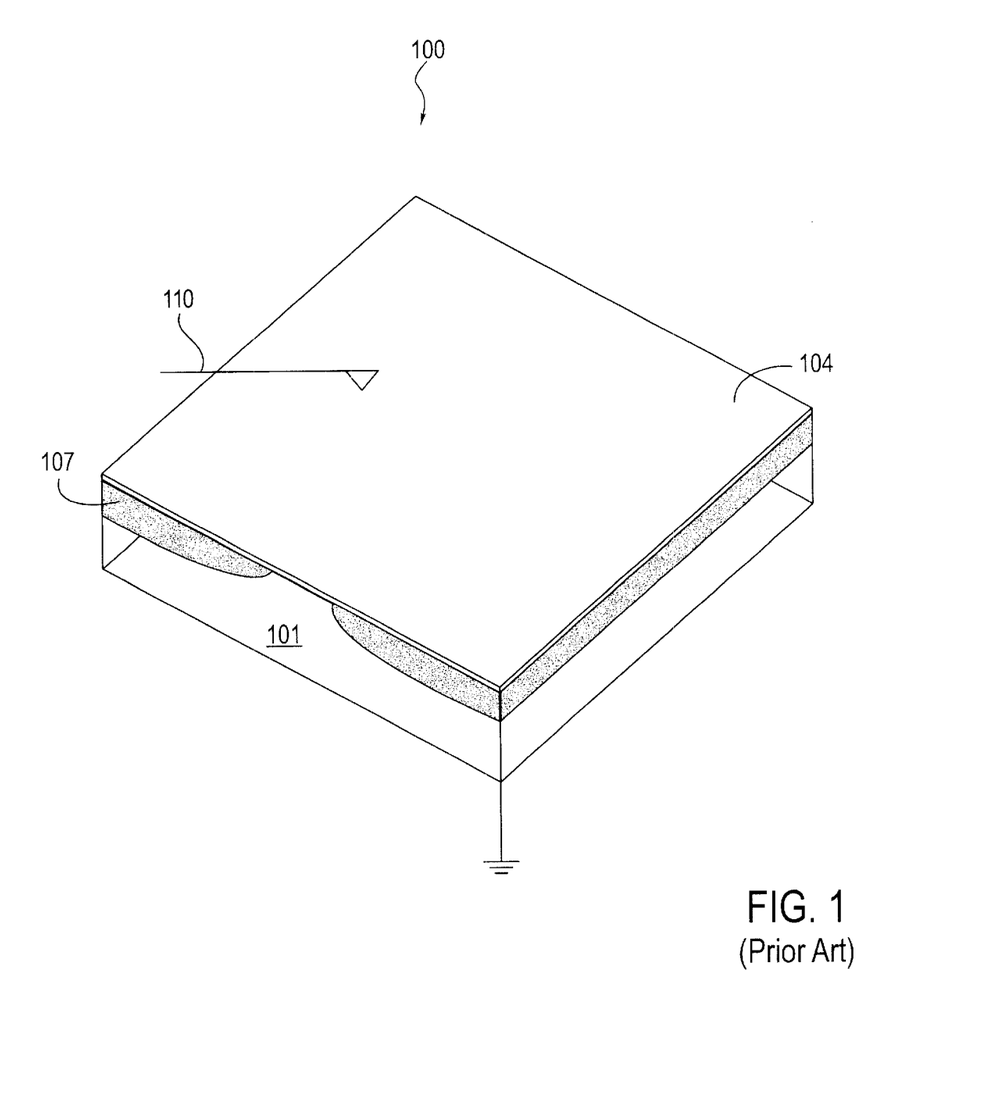
FIG. 1 shows a typical surface SCM imaging process.

Scanning Capacitance Microscopy has been conventionally used to image electrical charge populations in two spatial dimensions on the surface of a sample as shown in FIG. 1.

A sample or substrate 101 having a top or principal surface is placed onto an AFM/SCM stage and electrically grounded to said stage. Said sample 101 may have electrical charge concentrations that vary spatially in three dimensions, as represented by region 107. All materials and films on said top surface of sample 101 are removed, and a thin oxide film 104 is formed by reacting substrate atoms with an oxygen ambient at elevated temperature. Said oxide film provides a dielectric material between the SCM measurement apparatus and the sample 101 being measured.

Said SCM measurement apparatus includes a measurement tip 110 having a near-atomically sharp point. Said measurement tip is placed in near contact with oxide film 104. A high frequency electronic circuit varies the electrical potential on the measurement tip 110, while a high-frequency capacitance sensor monitors the change in capacitance versus the changing potential. From this measurement, electrical carrier concentrations are inferred using standard theoretical models.

Said measurement tip 110 is scanned in two dimensions relative to sample, while near contact condition is maintained by conventional AFM methods. Electrical charge concentration is calculated at each spatial scan point by measuring the change in capacitance versus potential and calculating the corresponding electrical charge concentration.

Conventional Depth Profiling Attempts

Figure 2:
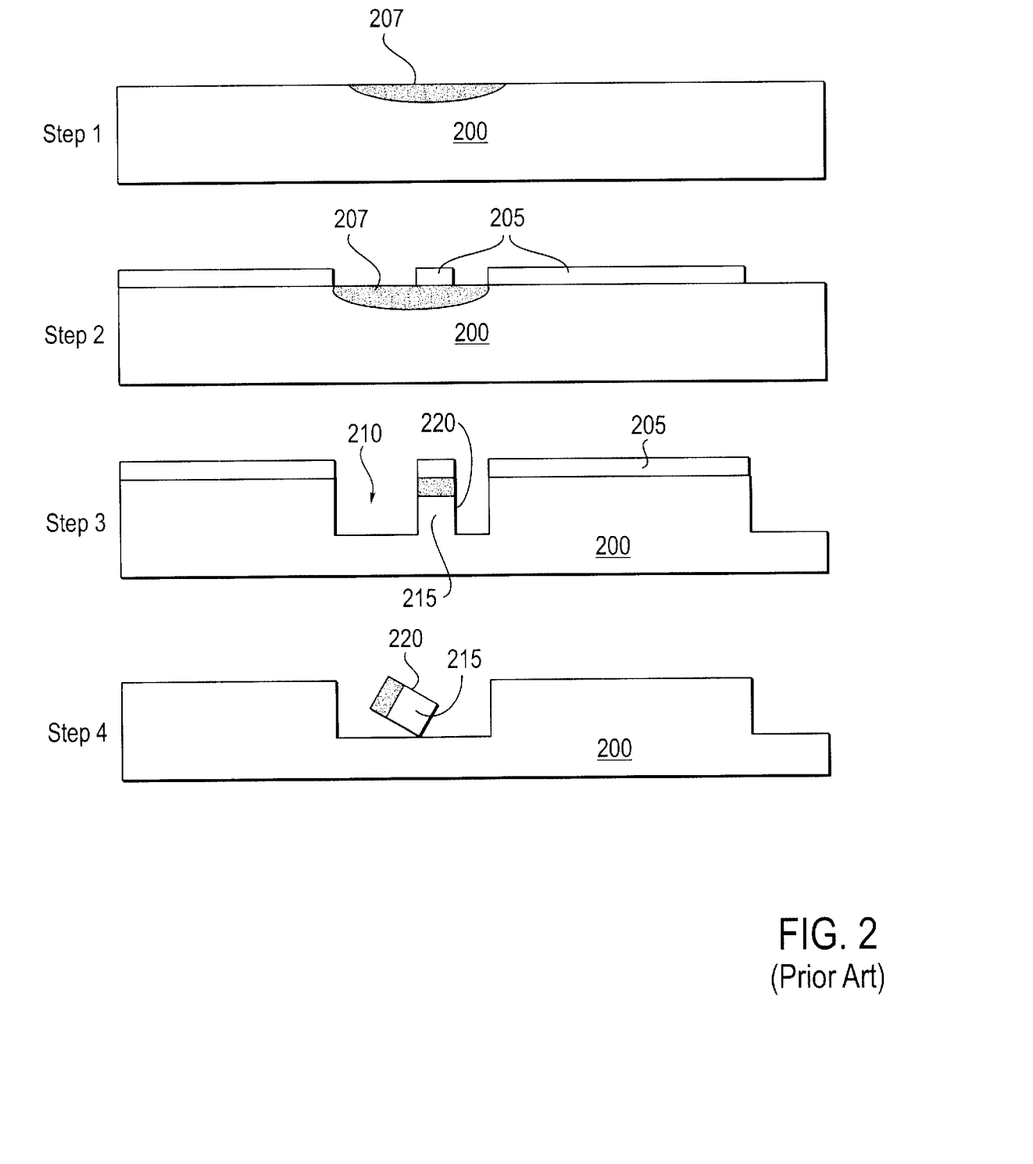
FIG. 2 shows a conventional approach to SCM imaging in the depth dimension.

In an attempt to gain access to electrical charge distributions in a dimension beyond the surface, various techniques have produced an orthogonal surface by cleaving or breaking the sample followed by mechanical polishing, or by plasma etching followed by toppling a resultant pillar. The latter technique is illustrated in FIG. 2. In Step 1 of FIG. 2, a starting sample or substrate 200 has spatially varying doping levels or electrical carrier concentrations, represented by a shaded region 207. In Step 2, an etch mask 205 is lithographically defined to select specific devices or regions on said sample 200. In Step 3, a physical etching process forms cavities or depressions 210 into sample 200 as defined by etch mask 205. Said cavities 210 form a post or pillar 215 having etched cross-sectional surface 220 substantially perpendicular to original sample surface. In Step 4, said pillar 215 is then mechanically toppled to rotate said cross-sectional surface 220 so that cross-sectional surface 220 may be accessed from a direction substantially similar to original sample surface. Once mechanically secured and electrically grounded, sample may then be placed onto a conventional SCM apparatus to obtain a cross-sectional SCM.

Atomically Smooth Cross-sectioning

Figure 3:
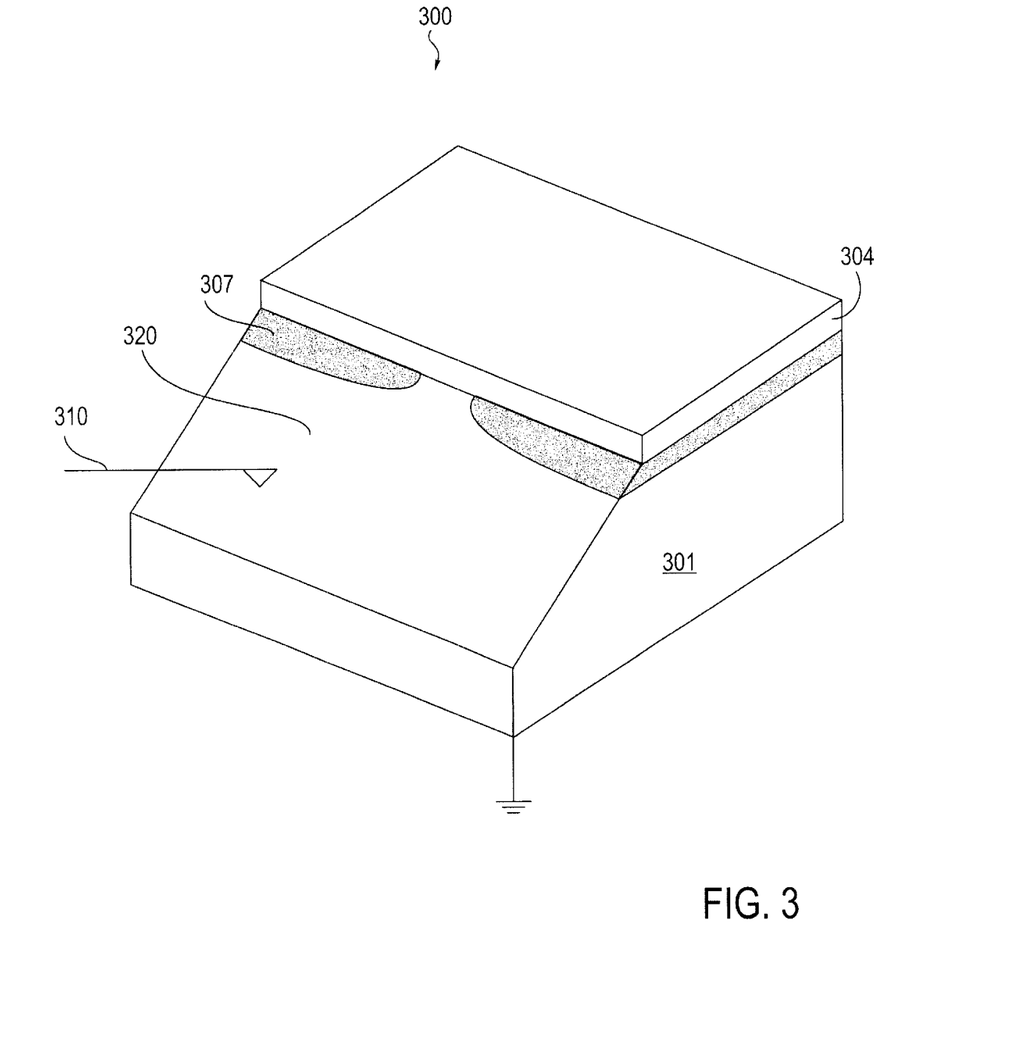
FIG. 3 shows a perspective view of an embodiment of the sample preparation technique in accordance with an aspect of the present invention.

One aspect of the present invention allows a substantially atomically smooth measurement surface, without having to mechanically topple, handle or secure small parts. FIG. 3 shows one embodiment of an aspect of the present invention for obtaining a substantially atomically smooth surface apart from the original surface of the sample.

A sample 301 having spatially varying doping or electrical carrier concentration (represented by shaded region 307) is masked by providing etch mask 304. Etch mask 304 may be patterned using conventional lithography. Top or principal surface of said sample 301 may need to be exposed in regions defined by said etch mask 304 by stripping layers of material previously deposited in the course of normal processing. Etch mask 304 is formed on sample 301 using techniques known to those skilled in the art. In one embodiment, etch mask 304 is composed of silicon nitride, though any lithographically patternable material could be employed if said material is substantially resistant to etch and polish chemistry used in subsequent crystal etching and polishing steps. Etch mask 304 is designed to expose portions of devices to be removed for cross-sectional analysis. Etch mask 304 may be designed to define many such regions across an entire wafer or substrate surface, thus exposing many devices to the etch process. Therefore it will be appreciated that many devices may be prepared simultaneously, without having to perform operations on any device individually. Separate similar devices may be cross-sectioned at different portions of each device to provide additional cross-sectional information. Devices need not be of the same type, size or geometry.

After etch mask 304 is defined on sample 301 top surface, an anisotropic chemical etch is performed on entire sample. Etching reactions are confined to areas previously defined by etch mask 304. Chemical etch is bounded in two dimensions by etch mask 304, and bounded in another dimension by crystallographic planes in sample 301. A new, substantially atomically smooth, cross-sectional surface 320 is formed by chemical etching. Said cross-sectional surface 320 is substantially coincident with a crystallographic plane of atoms which inhibits further chemical etching. The angle of cross-sectional surface 320 relative to original sample surface is determined by the crystal structure of sample 301. In a preferred embodiment, if sample 301 is <100> oriented silicon, and etch chemistry is selective to the <111>crystalline plane such as potassium hydroxide or tetra-methyl-ammonium-hydroxide based chemistry, then the angle between cross-sectional surface 320 and original sample surface is 54.7 degrees. Etch chemistry is known to those skilled in the art of micromachining and semiconductor processing. Various additives, concentrations of solutions, and etching temperatures are well characterized in public literature.

Once sample has been chemically etched, and cross-sectional surface 320 is formed on one or more devices or areas, a chemical or electrochemical polish may be used to achieve improvements in cross-sectional surface 320 smoothness. In one embodiment, ammonium fluoride is used to remove small asperities on cross-sectional surface 320 following chemical etch. J. Flidr, et. al., "Extracting site-specific reaction rates from steady state surface morphologies: kinetic monte carlo simulations of aqueous Si <111> etching," *J Chem. Phys.*, 108, 5542 (1998) is one recent study incorporated herein by reference. Surface roughness has been measured at less than 3 nm root-mean-square (RMS) roughness following ammonium fluoride polish.

After a substantially atomically smooth surface is achieved on cross-sectional surface 320, one embodiment might include a dielectric material provided on cross-sectional surface to facilitate an electrical measurement such as SCM. Said dielectric material may be deposited, grown or formed at any time after cross-sectional surface is formed. A gaseous ambient could constitute the dielectric material. Various annealing techniques known to those skilled in the art may be employed to improve the electrical characteristics of the dielectric material or interface with cross-sectional surface. In a preferred embodiment, a forming gas anneal comprising an ambient of a gas mixture of substantially hydrogen and nitrogen is used to reduce or eliminate extraneous charges at or near the interface between dielectric material and the cross-sectional surface.

Sample 301 is then placed on a conventional SCM stage with appropriate electrical grounding, and a conventional SCM procedure is applied to cross-sectional surface 320. In one embodiment, SCM tip 310 is scanned in two dimensions. A change in capacitance is measured for changing electrical potential at each scan point. Capacitance versus potential information is converted mathematically to obtain a true and accurate representation of the electrical charge concentrations at each scan point.

In an alternate embodiment, after sample 301 is anisotropically etched, a dopant-selective etch is applied to sample 301, specifically to surface 320, such that a topographic contour representative of doping concentrations results. The resultant topography is then mapped by conventional atomic force microscopy (AFM) and correlated to doping concentration. A technique for dopant selective etching is described in U.S. Pat. No. 5,520,769, and is incorporated herein by reference.

Nearby Electrical Ground

Figure 4:
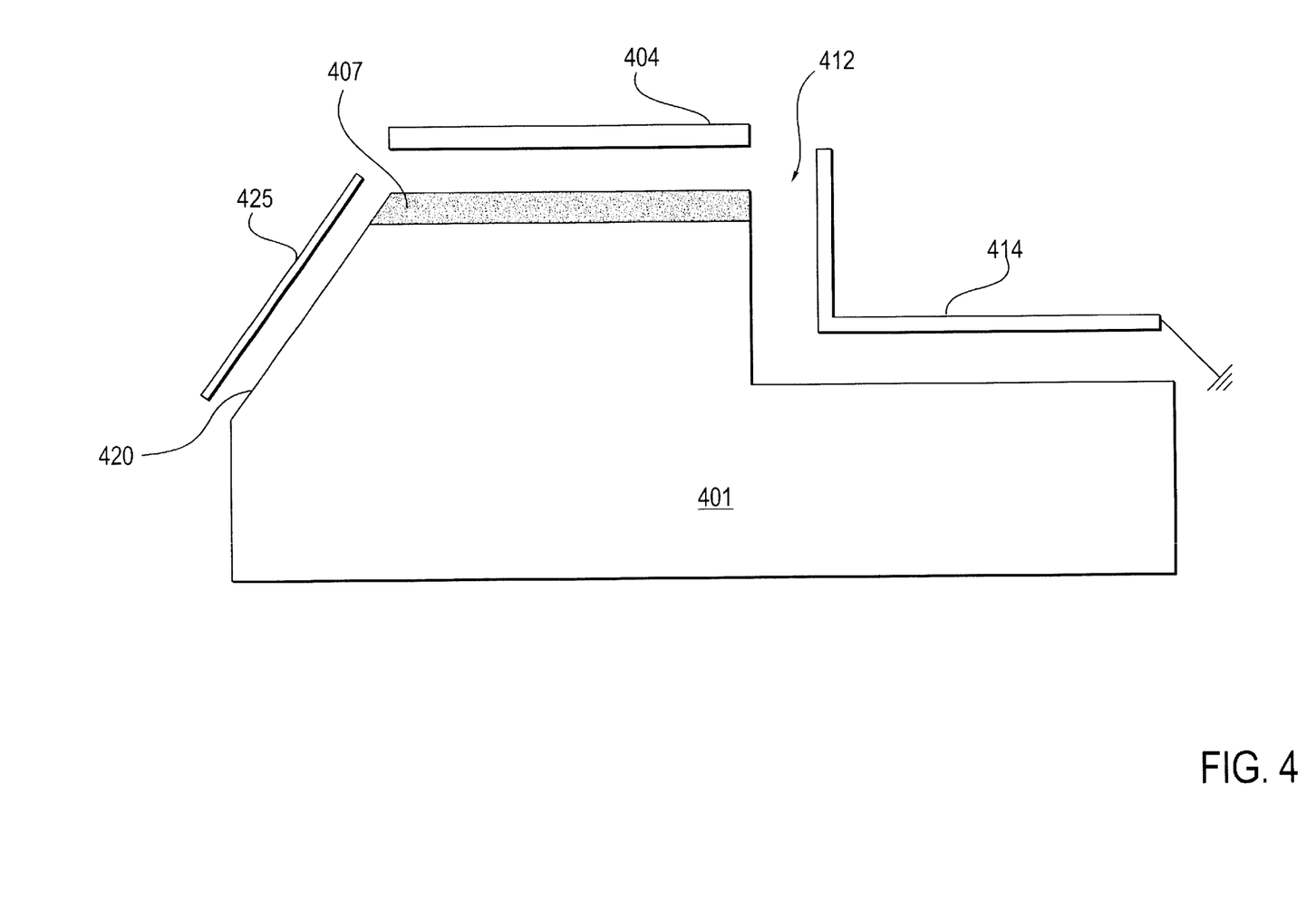
FIG. 4 is an exploded side-view of an embodiment of the present invention to provide a nearby electrical ground by conventional etching.

In one embodiment of the present invention, a nearby electrical ground is provided as illustrated in FIG. 4. A short path between the measured region and the electrical ground reduces the resistance to electrical current flow, providing a smaller resistance-capacitance (RC) product. Providing a nearby electrical ground reduces parasitic RC delays and improves quality and clarity of image data. Sample 401 with etch mask 404 is patterned to provide open windows above device to be cross-sectioned. Anisotropic etching is performed on sample to form cross-sectional surface 420. A second etch mask is deposited and an opening is formed in said second etch mask nearby to cross-sectional surface 420 so that cavity 412 may be formed by an etching process. It will be appreciated that the order of the steps used in forming cavity 412 and cross-sectional surface 420 may be reversed. An electrical ground contact 414 is formed in cavity 412 to provide a nearby electrical ground such that electrical path length is minimized. A dielectric material 425 may be formed on said cross-sectional surface 420 by chemical or physical deposition, or by a reaction of surface with a chemical ambient such as thermal oxidation. Said dielectric material 425 may be formed at any time after cross-sectional surface 420 is formed.

Figure 5:
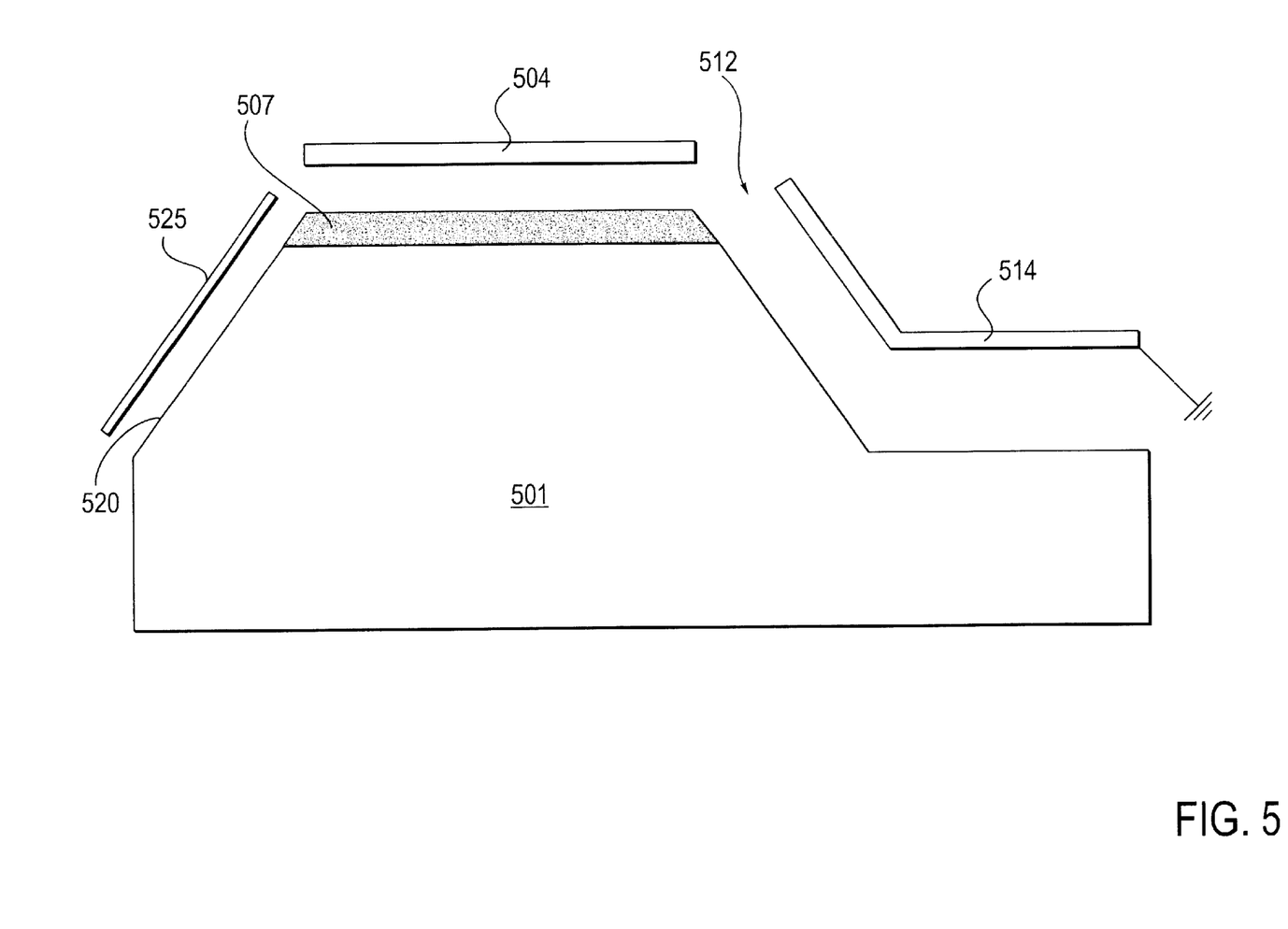
FIG. 5 is an exploded side-view of an embodiment of the present invention to provide a nearby electrical ground by anisotropic etching.

A preferred embodiment is illustrated in FIG. 5, wherein a single etch mask and single etch process can be used to form cross-sectional surface 520 and electrical ground cavity 512. Sample 501 is provided with etch mask 504 on top surface of said sample, and windows or openings are formed in desired cross-section area and nearby electrical ground region. An anisotropic etch forms cross-sectional surface 520 and said electrical ground cavity 512 simultaneously, using only one etch mask. An electrical ground contact 514 is formed in electrical ground cavity 512 such that a nearby electrical ground is provided for measurement of cross-sectional surface 520. A dielectric material 525 may be formed on said cross-sectional surface 520 by chemical or physical deposition, or by a reaction of surface with a chemical ambient such as thermal oxidation. Said dielectric material 525 may be formed at any time after cross-sectional surface 520 is formed.

Figure 6:
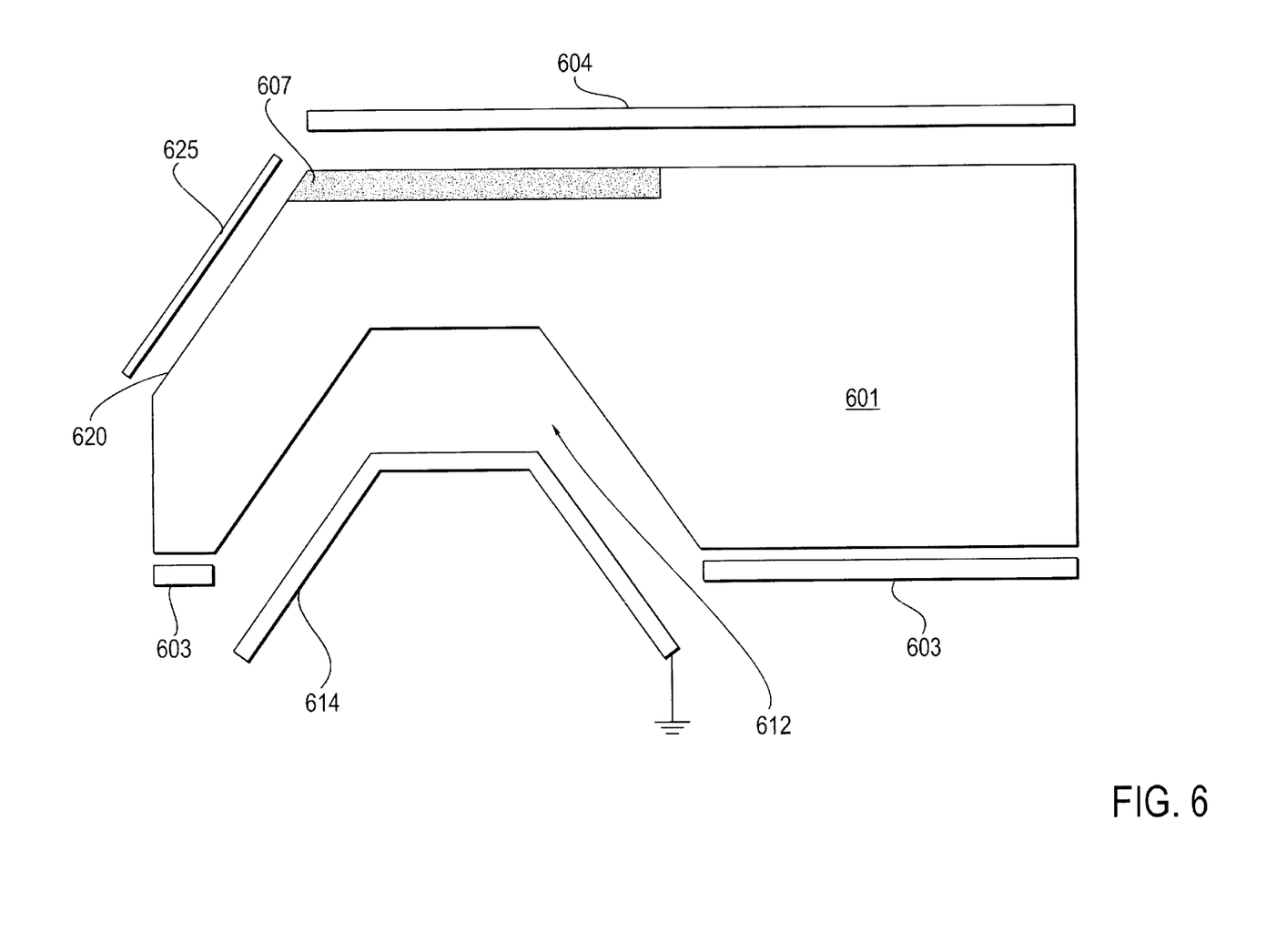
FIG. 6 is an exploded side-view of an embodiment of the present invention to provide a nearby electrical ground by backside etching or thinning.

Another embodiment for providing a nearby electrical ground contact is illustrated in FIG. 6, wherein said electrical ground contact is formed by etching or thinning the sample 601 from bottom surface or backside of said sample. An etch mask 604 is patterned on top surface of said sample 601. In a preferred embodiment, a backside etch mask 603 is also provided on the bottom surface, with an opening substantially near areas being cross-sectioned. An anisotropic etch forms cross-sectional surface 620 while simultaneously forming cavity 612. Openings in etch mask 603 and backside etch mask 604 can be dimensionally sized such that etch will self-stop on crystalline planes without etching through to the opposite side of the sample. It will be appreciated that the etch process used to form cavity 612 need not be simultaneous with the anisotropic etch used to form cross-sectional surface 620. Additionally, the etch process used to form cavity 612 need not be of the same etch chemistry or type of etch process as the etch process used to form cross-sectional surface 620. A nearby electrical ground contact 614 is then formed in cavity 612. A dielectric material 625 may be provided on cross-sectional surface 620. Said dielectric material 625 may be deposited, grown or formed at any time after cross-sectional surface 620 is formed. In another embodiment, entire bottom surface of sample 601 may be polished, etched or thinned without patterning in order to provide an improved electrical ground by locating electrical ground contact closer to the area being measured.

While the above discussion relates more directly to one embodiment of preparing a sample for scanning capacitance microscopy, it is recognized that the aforementioned sample preparation technique can be used to cross-section any crystalline sample to produce a substantially atomically smooth plane for various analysis techniques known to those skilled in the art.

Deconvolution Technique

Figure 7:
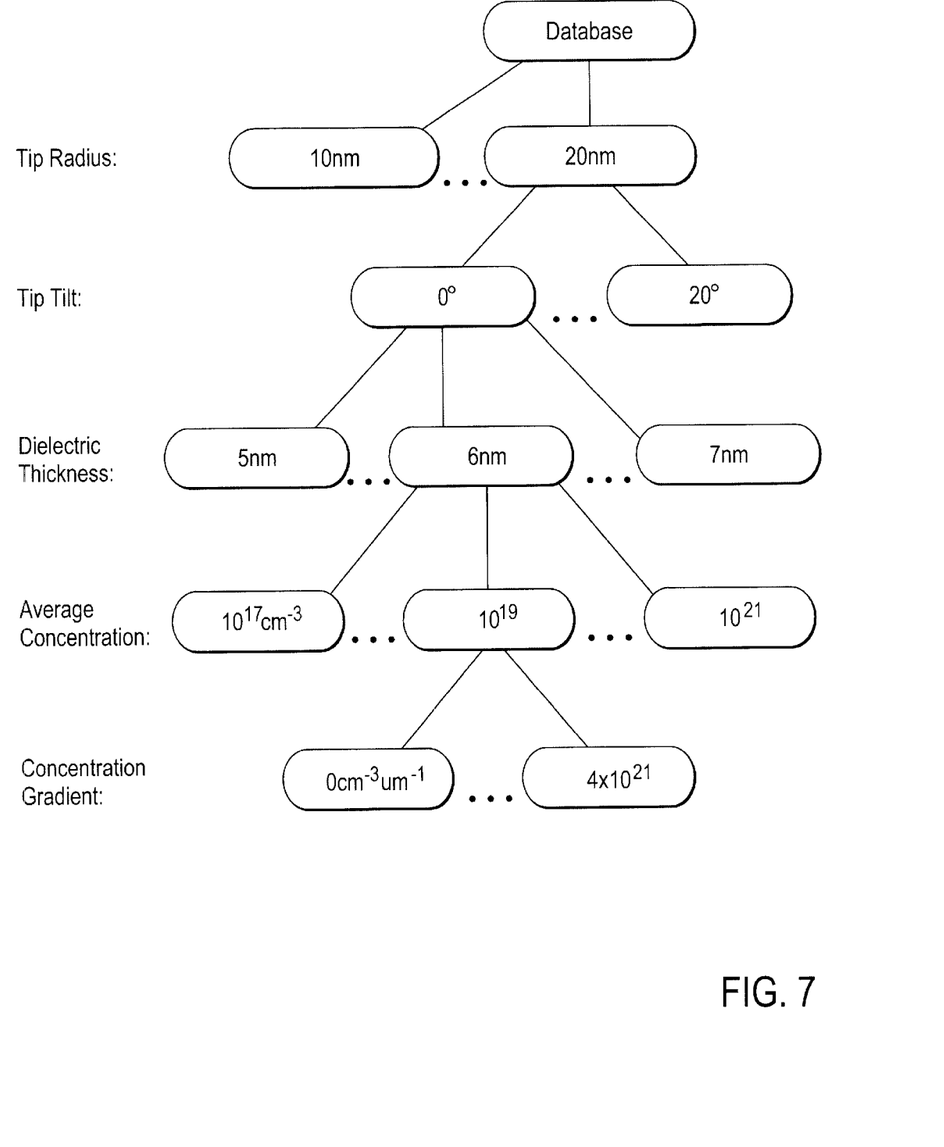
FIG. 7 is a diagram showing a database approach to dopant profile deconvolution in accordance with an aspect of the present invention.

FIG. 7 shows a database approach to deconvolving electrical charge concentrations from measured dC/dV data. Descriptive structure parameters are listed in the left column, with several discrete numerical choices for each parameter. FIG. 7 is simplified to indicate a populated range of each parameter for this example, but is not intended to limit the possible range of values for each said parameter. Each node in the database contains a theoretically calculated or simulated SCM electrical response for the structure parameters defining that node.

Once real two-dimensional SCM data is measured from a sample at one or more tip DC bias voltages, said database is searched iteratively to match or extrapolate to the measured data.

Figure 8:
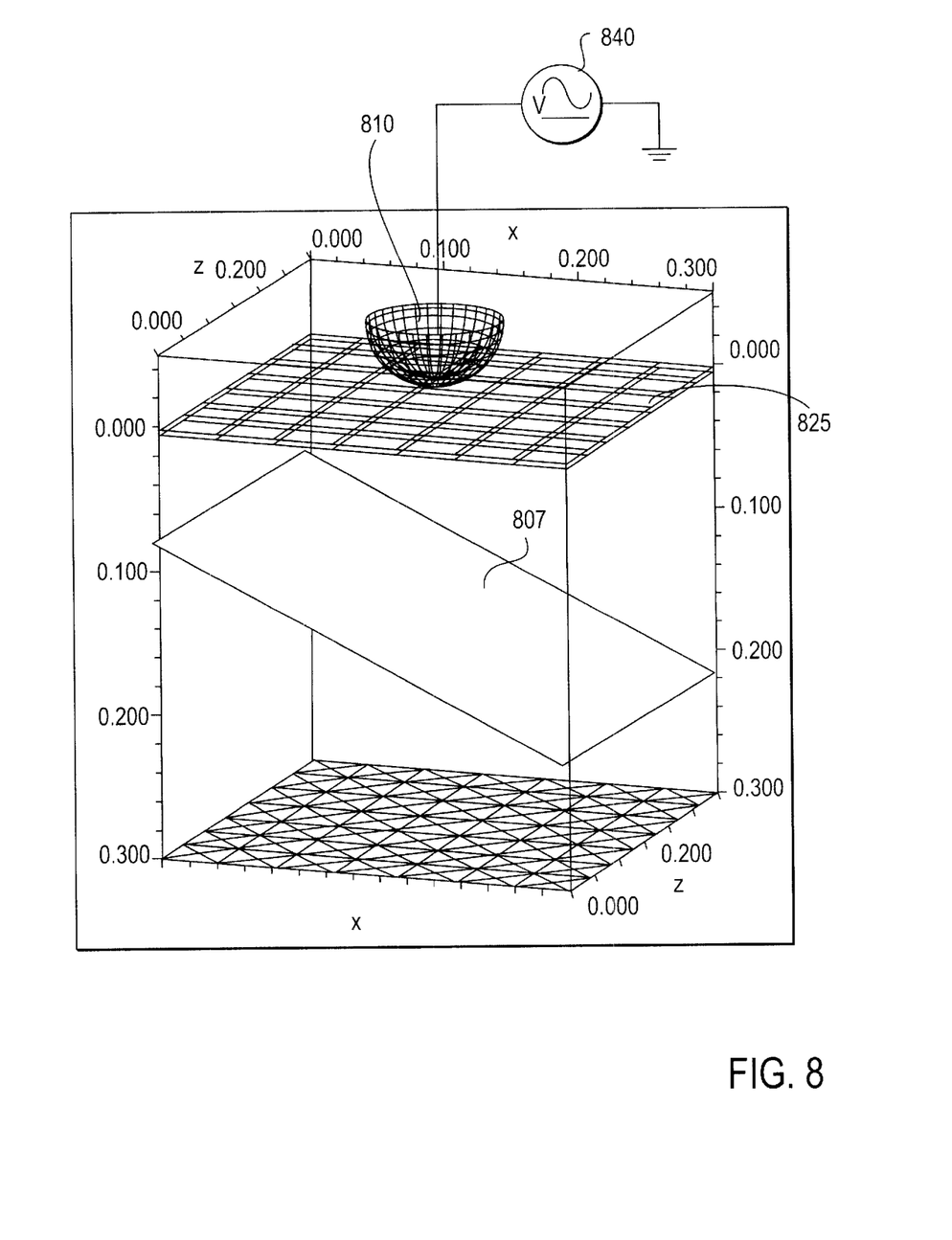
FIG. 8 is an electrical simulation structure used to populate a database with theoretical SCM responses for varying structure parameters.

The database is populated with theoretical SCM electrical responses by simulating a unique structure for each node in the database. Each structure has a unique set of parameters for the set consisting of SCM tip radius, tip angle or tilt, oxide thickness, average dopant concentration, doping gradient and tip DC bias. A simulation structure for a single node is shown in FIG. 8. One or more structures for each node can be simulated in a conventional electrical device simulator implementing known electrostatic phenomena, such as the "Davinci" simulator by Technology Modeling Associates, Inc., previously cited. FIG. 8 is a printout from the Davinci program. The three-dimensional simulation grid incorporates a dopant concentration gradient represented by contour 807, a dielectric material 825, an SCM probe 810 with finite tip radius and angular placement relative to surface being measured. A simulated potential is applied to probe 810 by voltage source 840, which comprises a high-frequency alternating-current (AC) voltage with a direct-current (DC) offset.

In one embodiment, said electrical device simulator solves the following partial differential equations in three dimensions for electrostatic potential, $\Psi$, electron concentration, n, and hole concentration, p:

$$\epsilon \cdot \nabla^2 \psi = -q(p-n+N_D^+ - N_A^-) - \rho_s$$

$$\frac{\partial n}{\partial t} = \frac{1}{q} \nabla \cdot J_n - U_n$$

$$\frac{\partial p}{\partial t} = \frac{1}{q} \nabla \cdot J_p - U_p$$

For each unique set of structure parameters, a simulated SCM electrical (dC/dV) response is generated, and cataloged in the database. Each node in the database is populated with a simulated response. Simulated responses at each node may not be substantively unique, which requires the deconvolution algorithm to consider data from neighboring scan pixels in deciding on the proper database match.

Improving Computer Simulation Models

Semiconductor devices and processes are commonly designed using computer simulators, which implement physical or empirical models. These models are usually developed or improved by building devices or test samples, measuring physical properties of these devices or samples, and then providing the measured information to a computer simulator. That information is stored in a simulator by either providing a physical model to describe the observed behavior, or providing a database that catalogs the observed behavior with process and device parameters. In either case, a simulator that can predict device parameters before a new type of device is actually built is highly desirable.

When a new type of device is postulated, the fabrication and operation of the device are simulated to test feasibility, refine the manufacturing process and optimize the device performance before actually building it. This offers potentially substantial cost and time savings in bringing a new type of device to market. Once the device is actually constructed, it may not work properly, even though a simulator may have predicted that it should. Such a situation arises when simulation programs do not accurately predict the reality of the device operation or construction because the models implemented in the program are incorrect or inadequate. This requires modification of the manufacturing process, and one or more additional fabrication attempts. For each iteration of the design loop, measured information is provided to the simulator for the purpose of correcting models or creating new models such that the simulator makes a more accurate prediction. If, on the other hand, a simulator contains adequate models to simulate the device being designed, then first pass manufacturing success may occur, but models will still likely be adjusted based on any new information learned from the manufacture of the new device.

Errors or inadequacies in simulation models often arise because certain phenomena have not been observable or quantifiable with conventional measurement techniques. An aspect of the present invention provides a method for measuring previously unobserved phenomena in sub-micron devices, and a method for correcting conventional models to accurately predict physical behavior in the manufacturing process and device operation.

Figure 9:
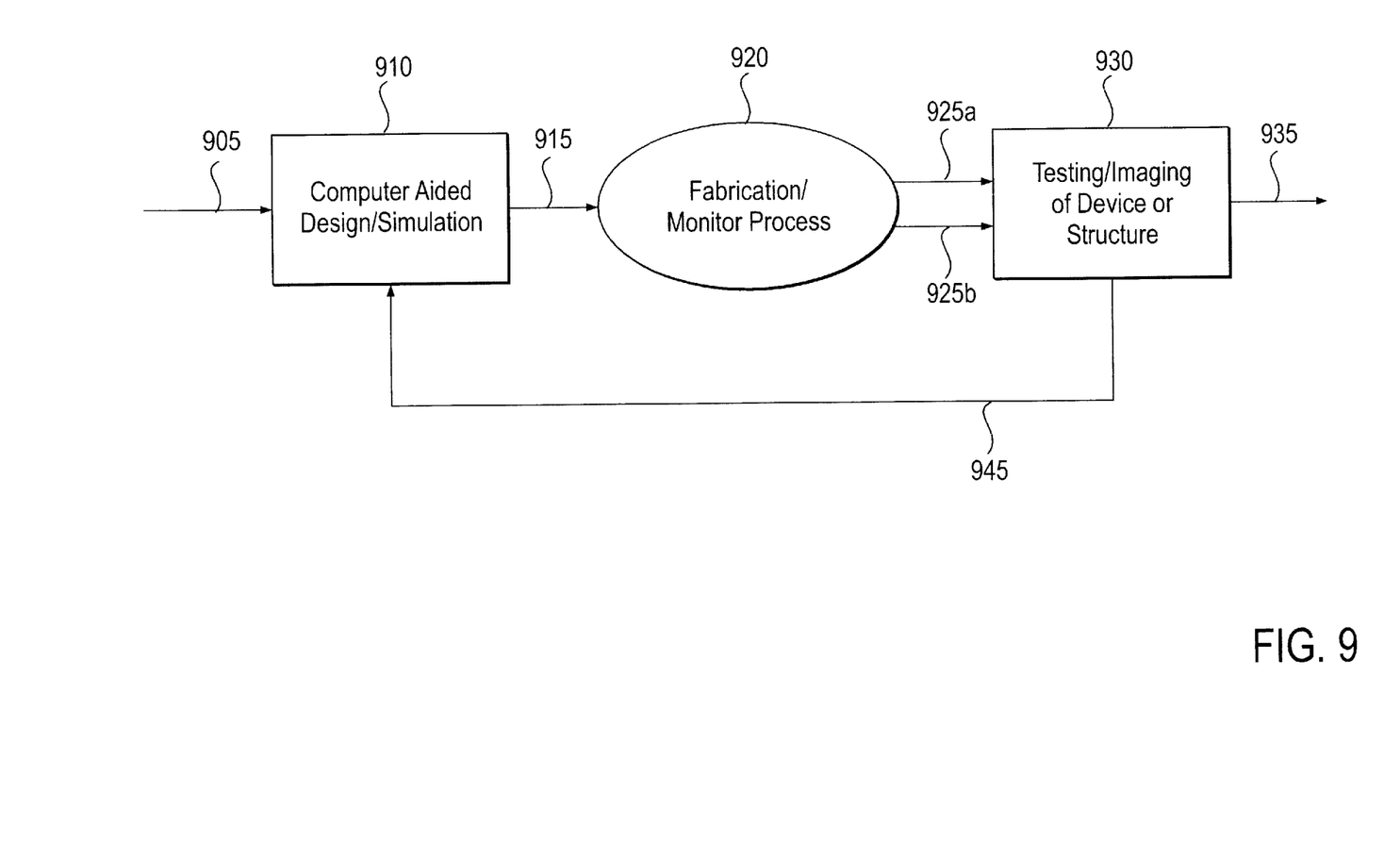
FIG. 9 is a block diagram showing a system used to develop models and improvements for devices and processes in accordance with an aspect of the present invention.

FIG. 9 is a diagram showing how an aspect of the present invention is used to improve or create computer simulation models. A new or improved device is postulated, and a description 905 is applied to computer simulator 910. Said simulator 910 comprises one or more computer programs interacting to simulate and model the manufacture or the operation of said device, and embodies models, design rules and process parameters. Simulator 910 is used interactively by designer to learn about the manufacture and operation of the device, and to make changes to design for better performance, higher manufacturing yield, and increased chances of successful operation on the first construction attempt. Once a designer is satisfied that the device and manufacturing process are optimized for the intended use, process and design specifications 915 are transferred to a fabrication facility 920, wherein the device is manufactured according to the process and design specifications 915. An aspect of the present invention may be employed in fabrication facility 920 for purposes of monitoring the fabrication process, and providing useful feedback of information about the process. A finished device 925a, and in-situ information 925b noted during the fabrication process are transferred to a testing facility 930, wherein an aspect of the present invention is used to inspect devices for operation, performance and conformance to process and design specification 915. Working devices 935 may result. Feedback information 945, comprising information regarding inspected devices from testing facility 930 and in-situ information 925b from fabrication facility 920, is transferred back to simulator 910 for comparison to and adjustment of models, design rules and process parameters used in first simulating new device design.

An aspect of the present invention enables new and improved devices to be designed and fabricated by providing previously unattainable feedback information to simulator 910. Closer tolerances and finer design rules can be adopted since an aspect of the present invention allows greater control over manufacturing tolerances. Spatial overlap of key device features, for instance transistor gate overlap of source and drain, reduces parasitic capacitance, therefore increases device performance. Separation between devices can be reduced, increasing overall circuit density and decreasing cost. Using design rules modified by an aspect of the present invention, new lithography masks can be produced to manufacture smaller, higher performance, faster-switching circuits. An aspect of the present invention will enable devices and with critical dimensions below 100 nm to be designed and built. Scanning probe techniques show promise for spatial resolutions suitable for 10 nm devices, to which an aspect of the present invention could be applied.

Figure 10:
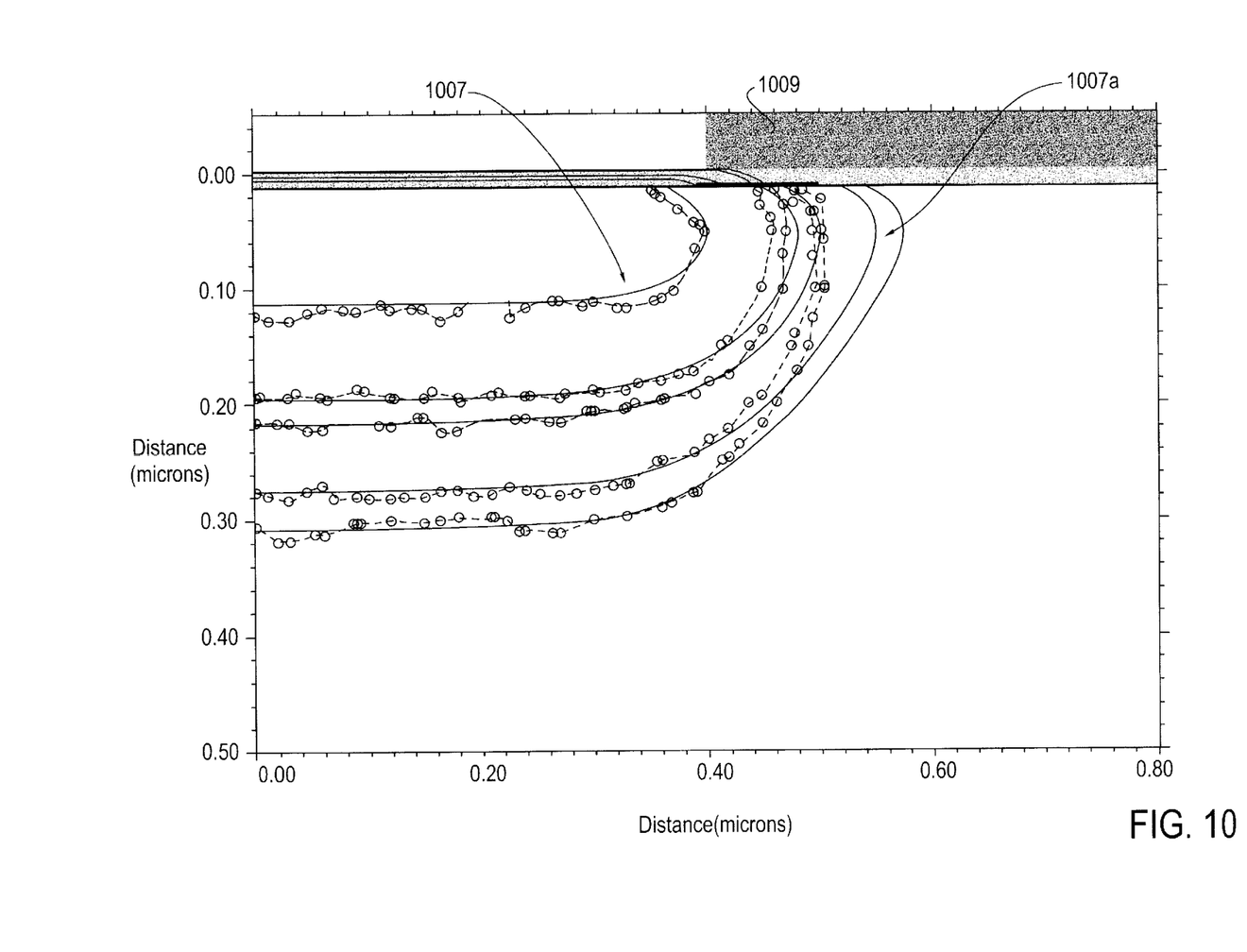
FIG. 10 is an output from a semiconductor process simulator comparing data measured with the present invention to conventional models.

FIG. 10 shows output from a computer simulator 910 representing dopant contours 1007 from the source region of a typical submicron transistor having gate 1009. Solid lines are those simulated using models, design rules, and process parameters in use by the simulator prior to the manufacture of the actual device 935. Data points (circles and dashed lines) are measured using an aspect of the present invention from device 935 after manufacture. Information 945, comprising dopant contours in this example, is fed back to simulation program 910 to update models, design rules, and process parameters. In this instance, doping information in the depth direction was reasonably predicted, but lateral placement of dopant under transistor gate 1009 in region 1007a shows significant error. Such error prompts an update in process parameters (for instance, the angle or energy of ion implant), ion implant and diffusion models (for instance, lateral straggle of implanted species), and design rules (for instance, the placement of the gate or sidewall spacer for ion implantation). Such modified process parameters, models and design rules lead to improvement in simulation of the next generation of devices that are designed using simulation program 910 implementing the modifications.

While the invention has been described in connection with what are presently considered to be the most practical and preferred embodiments, it is to be understood that the invention is not limited to the disclosed embodiments, but rather is intended to cover various modifications, equivalent arrangements, various scanning probe techniques and other analysis techniques which are included with the spirit and scope of the following claims.

We claim:

1. A process for preparing a crystalline substrate sample having a principal surface for precise measurement of electrical properties, such as electrical carrier concentration, in that sample comprising:

providing an etch mask material on one or more areas on the crystalline substrate;

selecting one or more said areas for analysis;

lithographically patterning one or more openings in said etch mask material across the selected areas;

anisotropically etching into said selected areas, wherein the anisotropic etch stops on a crystalline plane of said crystalline substrate to provide an atomically smooth cross sectional measurement face;

applying scanning capacitance measurement to said atomically smooth cross-sectional measurement face to obtain a representation of a spatial distribution of electrical properties, such as electrical carrier concentration, in one or more dimensional axes defined on the measurement face;

trigonometrically scaling at least one of the dimensional axes to create an image that is representative of an orthogonal cross-section to provide a representation of electrical properties, such as electrical carrier concentrations, beneath the original sample surface in up to three dimensions.

2. A method for determining a property of a material with respect to at least two dimensions, comprising the steps of:

providing one or more areas on a crystalline substrate having a principal surface with an etch mask material provided on said principal surface;

selecting one or more said areas for analysis;

lithographically patterning one or more openings in said etch mask material across the selected areas;

anisotropically etching into said selected areas wherein the anisotropic etch stops on a crystalline plane of said crystalline substrate, such that a substantially atomically smooth cross-sectional surface results;

measuring a material property from said atomically smooth cross-sectional surface to thereby obtain a true representation of said material property by moving a fine tip in close proximity to said cross-sectional surface of said crystalline substrate within a predetermined scan area;

relating said measured data according to a predetermined relationship to derive said material property at each of the locations, whereby data for said material property is provided with respect to at least two dimensions in the region of said scan.

3. A process for preparing a sample for precise measurement of electrical properties comprising:

providing one or more areas on a crystalline substrate having a principal surface with an etch mask material provided on said principal surface;

selecting one or more of said areas for analysis;

lithographically patterning one or more openings in said etch mask material across the selected areas;

anisotropically etching into said selected areas wherein the anisotropic etch stops on a crystalline plane of said crystalline substrate, forming a substantially atomically smooth cross-sectional surface in each said selected area;

lithographically patterning and etching one or more regions near said selected areas and forming an electrical contact in said regions such that a nearby electrical ground is provided to improve electrical measurement;

applying electrical measurement to said atomically smooth cross-sectional surface to thereby obtain a true representation of a spatial distribution of electrical properties in one or more dimensions.

4. A process for preparing a sample for precise measurement of electrical properties comprising:

providing one or more areas on a crystalline substrate having a principal surface with an etch mask material provided on said principal surface;

selecting one or more of said areas for analysis and selecting a region nearby each selected area;

lithographically patterning a plurality of openings in said etch mask material across said selected areas and across said nearby regions;

anisotropically etching into selected areas and said nearby regions wherein the anisotropic etch stops on crystalline planes of said crystalline substrate, forming substantially atomically smooth cross-sectional surfaces which cross-section said selected areas and said nearby regions;

forming one or more electrical contacts in each said nearby region such that a nearby electrical ground is provided to reduce electrical resistance of said ground and thereby improve electrical measurement;

applying electrical measurement to said atomically smooth cross-sectional surfaces to thereby obtain a true representation of a spatial distribution of electrical properties in one or more dimensions.

5. A process for preparing a sample for precise measurement of electrical properties comprising:

providing one or more areas on a crystalline substrate having a principal surface and a secondary surface with an etch mask material provided on one or more surfaces of said crystalline substrate;

selecting one or more of said areas for analysis;

lithographically patterning one or more openings in said etch mask material across the selected areas;

anisotropically etching into said selected areas wherein the anisotropic etch stops on crystalline planes of said crystalline substrate, forming substantially atomically smooth cross-sectional surfaces which cross-section said selected areas;

thinning or etching of said substrate or a region of said substrate near said selected areas and forming an electrical contact thereon such that a nearby electrical ground is provided to improve electrical measurement;

Applying electrical measurement to said atomically smooth cross-sectional surface to thereby obtain a true representation of a spatial distribution of electrical properties in one or more dimensions.

6. A method for deconvolving sensed Scanning Capacitance Microscopy (SCM) data into electrical charge concentration data wherein the deconvolution method comprises a database populated with theoretical capacitance versus voltage responses for local structure parameters, said database comprising:

an SCM sensing tip placed at an angle relative to a surface normal;

a non-zero spatial concentration gradient in electrical charge distribution in one or more dimensions;

an average concentration of electrical charge;

a non-zero radius of the sensing tip point;

a capacitance due to said dielectric material;

a direct-current (DC) bias voltage applied to said sensing tip; such that said deconvolution comprises iteratively searching said database to derive actual structure parameters from said sensed SCM values.

7. A process for preparing a sample for precise measurement of electrical properties comprising:

providing one or more areas on a crystalline substrate having a principal surface with an etch mask material provided on said principal surface;

selecting one or more said areas for analysis;

lithographically patterning one or more openings in said etch mask material across the selected areas;

anisotropically etching into said selected areas wherein the anisotropic etch stops on a crystalline plane of said crystalline substrate, such that a substantially atomically smooth cross-sectional surface results;

applying electrical measurement to said atomically smooth cross-sectional surface to thereby obtain a true representation of a spatial distribution of electrical properties in one or more dimensions, wherein said electrical measurement includes Scanning Capacitance Microscopy to measure active dopant concentrations in the range from $1 \times 10^{15}$ to $5 \times 10^{21}$ per cubic cm., and wherein said anisotropic etch is followed by a chemical or electrochemical polish such that surface properties of said cross-sectional surface are improved.

8. A process for preparing a sample for precise measurement of electrical properties comprising:

providing one or more areas on a crystalline substrate having a principal surface with an etch mask material provided on said principal surface;

selecting one or more said areas for analysis;

lithographically patterning one or more openings in said etch mask material across the selected areas;

anisotropically etching into said selected areas wherein the anisotropic etch stops on a crystalline plane of said crystalline substrates such that a substantially atomically smooth cross-sectional surface results;

applying electrical measurement to said atomically smooth cross-sectional surface to thereby obtain a true representation of a spatial distribution of electrical properties in one or more dimensions, and wherein a dielectric material is placed into contact with said cross-sectional surface to facilitate or improve said electrical measurement, such that placement of said dielectric material is followed by a thermal treatment in an ambient designed to improve electrical properties at interface between said cross-sectional surface and said dielectric film, such as a forming gas anneal.

* * * * *